US005229490A

United States Patent [19]

Tam

[11] Patent Number: 5,229,490

[45] Date of Patent: Jul. 20, 1993

[54] MULTIPLE ANTIGEN PEPTIDE SYSTEM

[75] Inventor: James P. Tam, New York, N.Y.

[73] Assignee: The Rockefeller University, New York, N.Y.

[21] Appl. No.: 631,185

[22] Filed: Dec. 20, 1990

Related U.S. Application Data

[63] Continuation of Ser. No. 336,845, Apr. 12, 1989, abandoned, which is a continuation of Ser. No. 68,840, Jun. 30, 1987, abandoned, which is a continuation-in-part of Ser. No. 47,204, May 6, 1987, abandoned.

[51] Int. Cl.[5] .......................... C07K 7/02; C07K 7/08; C07K 7/10; A61K 39/385

[52] U.S. Cl. .................................... 530/324; 530/325; 530/323; 530/326; 530/327; 530/328; 530/345; 530/403; 530/405; 530/409; 424/88; 424/89; 424/92; 930/30; 930/210; 930/221

[58] Field of Search ............... 530/323, 324, 326, 327, 530/345, 405, 325, 328, 409, 403; 514/13, 12, 14, 15, 21; 424/88, 92, 89; 930/30, 210, 221

[56] References Cited

U.S. PATENT DOCUMENTS

| | | | |
|---|---|---|---|
| 4,289,872 | 9/1981 | Deukewalter et al. | 528/328 |
| 4,515,920 | 5/1985 | Erickson | 525/54.11 |
| 4,707,357 | 11/1987 | Dame et al. | 424/88 |
| 4,713,366 | 12/1987 | Stevens | 514/13 |

OTHER PUBLICATIONS

Aharoni et al. (1982) Macromolecules 15:1093–1098.

Mitchell et al. (1982) in *Monoclonal Hybridoma Antibodis* CRC Press, Inc., Boca Raton, Fl. pp. 151–168.

Posnett et al. (1988) JBC 263(4):1719–1725.

Auriault et al. (1991) Peptide Res. 4(1):6–11.

*Primary Examiner*—Christine M. Nucker
*Assistant Examiner*—Kay K. Kim
*Attorney, Agent, or Firm*—Wyatt, Gerber, Burke and Badie

[57] ABSTRACT

Multiple antigen peptide systems are described in which a large number of antigens are bound to the functional groups of a dendritic core molecule providing a high concentration of antigen in a low molecular volume. The products are useful for producing chemically defined univalent or multivalent vaccines and in diagnostic tests.

33 Claims, 10 Drawing Sheets

MULTIPLE ANTIGEN PEPTIDE SYSTEM

RELATED APPLICATIONS

This application is a continuation of application Ser. No. 07/336,845 filed Apr. 12, 1989 which is in turn a continuation of application Ser. No. 07/068,840 filed Jun. 30, 1987. The latter is a continuation in part of application Ser. No. 07/047,204 filed May 6, 1987. All of these applications were commonly owned and are now abandoned.

Vaccines often comprise an antigen on a natural carrier such as a protein, a carbohydrate, a lipid or a liposome. Such vaccines are useful and have been employed for many years. There are however a number of art recognized problems with them. Several of these problems are related to the carrier. Since the carriers are isolated from natural sources, they are often not of uniform quality. Additionally, despite expensive and arduous purification efforts, it is difficult, and often impossible, to provide products completely free of natural contaminants. Such contaminants may themselves be antigenic. They cause the undesirable side reactions often associated with the use of vaccines, particularly fevers and tissue swelling. Additionally, the concentration of antigen may vary from one batch to another because the amounts of antigen which react with the carrier or are absorbed on its surface are not uniform.

Recently a new class of polymers has become known. They are characterized by higher concentrations of functional groups per unit of molecular volume than ordinary polymers. Generally, they are based upon two or more identical branches originating from a core molecule having at least two functional groups. Such polymers have been described by Denkewalter et al in U.S. Pat. No. 4,289,872 and by Tomalia et al in several U.S. Patents including U.S. Pat. Nos. 4,599,400 and 4,507,466. Other polymers of the class have been described by Erickson in U.S. Pat. No. 4,515,920. The polymers are often referred to as dendritic polymers because their structure may be symbolized as a tree with a core trunk and several branches. Unlike a tree, however, the branches in dendritic polymers are all substantially identical.

The products of this invention are based on such dendritic systems in which antigens are covalently bound to the branches which radiate from the core molecule. The system has been termed the multiple antigen peptide system and is sometimes referred to herein as MAPS. As will be apparent from the discussion hereinafter, some of the carrier or core molecules used to form the products of the invention are of a molecular weight such that they might not usually be regarded as polymers. However, since their basic structure is similar to dendritic polymers, it is convenient to describe them as such. Therefore the term "dendritic polymer" will be sometimes used herein to define the products of the invention. The term includes carrier molecules which are sufficiently large to be regarded as polymers as well as those which may contain as few as three monomers.

It has now been discovered that dendritic polymers can function usefully as carriers for a wide variety of antigens.

This invention will be better understood from a brief discussion of the structure of dendritic polymers.

Dendritic polymers are built upon a core molecule which is at least difunctional. Each of the functional groups on the core molecule form at least two branches, the principal units of which are also at least difunctional. Each difunctional unit in a branch provides a base for added growth.

The system can be better visualized by reference to specific molecules. If, for example, lysine with two amino groups is joined in a peptide bond through its carboxyl group to the amino group of alanine or glycine which may in turn be bound to a resin, the resulting molecule will have two free amino groups. This dipeptide may be regarded as the first generation. It may be joined to two additional lysine molecules by the formation of peptide bonds to produce a second generation molecule with four free amino groups. The process can be repeated to form third, fourth or even higher generations of products. With each generation the number of free amino groups increases geometrically and can be represented by $2^n$, where n is the number of the generation.

Although none of these compounds are of particularly high molecular weight, it is convenient to refer to them as dendritic polymers.

FIG. 1 shows a three generation dendritic polymer core molecule based on lysine in which each of the eight available amino groups are joined to a peptide antigen through a glycine linker molecule.

The same types of reactions can be carried out with aspartic or glutamic acid, both of which have two carboxyl groups and one amino group to produce polyaspartic or polyglutamic acids with $2^n$ free carboxyl groups.

The necessary chemistry for performing these types of synthesis is known and available. With amino acids the chemistry for blocking functional groups which should not react and then removing the blocking groups when it is desired that the functional groups should react has been described in detail in numerous patents and articles in the technical literature.

The dendritic polymers can be produced on a resin as in the Merrifield synthesis and then removed from the polymer.

Tomalia utilized ammonia or ethylenediamine as the core molecule. In this procedure, the core molecule is reacted with an acrylate ester by Michael addition and the ester groups removed by hydrolysis. The resulting first generation molecules contain three free carboxyl groups in the case of ammonia and four free carboxyl groups when ethylenediamine is employed. Tommalia extends the dendritic polymer with ethylenediamine followed by another acrylic ester monomer, and repeats the sequence until the desired molecular weight is attained. It will, however, be readily apparent to one skilled in the art, that each branch of the dendritic polymer can be lengthened by any of a number of selected procedures. For example, each branch can be extended by multiple reactions with lysine molecules.

Erickson utilized the classic Merrifield technique in which a polypeptide of substantially any desired molecular weight is grown from a solid resin support. As the technique is utilized for the preparation of dendritic polymers, the linking molecule which joins the polymer to the resin support is trifunctional. One of the functional groups is involved in the linkage to the resin, the other two functional groups serve as the starting point for the growth of the polymer. The polymer is removed from the resin when the desired molecular weight has been obtained. One standard cleavage procedure is treatment with liquid hydrogen fluoride at 0° C. for one hour. Another, and more satisfactory procedure, is to utilize a complex of hydrogen fluoride and dimethylsulfide (HF:DMF) as described by Tam et al in J. Am. Soc. (1983) 105: 6442. This procedure greatly minimizes side reactions and loss of peptide.

Denkewalter, in one example of his process, utilizes lysine as the core molecule. The amino groups of the core molecule are blocked by conversion to urethane groups. The carboxyl group is blocked by reaction with benzhydrylamine. Hydrolysis of the urethane groups generates a benzhydrylamide of lysine with two free amino groups which serve as the starting points for the growth of the dendritic polymer.

This brief outline of three of the available procedures for producing dendritic polymers should be adequate to teach those skilled in the art the basic principles of the current technology. They will also teach the skilled artisan the salient features of the polymers, one of the most important of which is that the polymers provide a large number of available functional groups in a small molecular volume. The result is that a high concentration of antigens in a small volume can be achieved by joining the antigen to those available functional groups. Moreover, the resulting molecular product contains a high proportion of antigen on a relatively small carrier. This is in contrast to conventional products used as a basis for vaccines. These conventional products often are composed of a small amount of antigen on a large amount of carrier.

Other important features of the dendritic polymer as an antigen carrier are that the exact structure is known; there are no contaminants which may be themselves antigenic, produce tissue irritation or other undesirable reactions; the exact concentration of the antigen is known; the antigen is symmetrically distributed on the carrier; and the carrier can be utilized as a base for more than one antigen so that multivalent vaccines can be produced. The principal advantage of the MAPS of this invention as the basis for vaccines is that unlike previous sytems using natural carriers such as keyhole limpet hemocyanin, tetanus toxoid and bovine serum albumin, the carriers of this invention are fully defined chemical entities on which the antigens are dispersed in known concentrations. Additionally, the antigen comprises a large part of the molecule not a relatively small and undefined proportion of the molecule as in the case of natural carriers.

When the MAPS is to be employed to produce a vaccine, it is preferred that the core molecule be a naturally occurring amino acid such as lysine so that it can be dealt with by the body following the usual metabolic pathways. However, as will be explained more fully hereinafter, amino acids which are not naturally occurring, even those which are not α-amino acids can be employed. The acids, or any other asymmetric molecules used in building the core molecule can be in either the D or L form.

Although the dendritic polymers have been principally described hereinabove as polyamide polymers, it will be readily apparent that the carriers of this invention are not limited to dendritic polyamides. Any of a wide variety of molecules having at least two available functional groups can serve as core molecules. Propylene glycol, for example, can serve as the basis for a polyester dendritic polymer. Succinic acid with selected glycols or amines can serve as a core molecule to generate polyesters or polyamides. Diisocyanates can be used to generate polyurethanes. The important point is that the core molecule has at least two available functional groups from which identical branches can be generated by sequential scaffolding type reactions with additional molecules also having at least two available functional or anchoring groups on each branch. In the most simple case in which the core molecule has two available functional groups and each succeeding generation has two available functional groups, the number of anchoring sites to which antigen molecules can be anchored is expressed by $(2)^n$ where n is the number of the generation.

For a more complete discussion of the chemistry of dendritic polymers attention is directed to Tomalia et al, Polymer Journal 17 (1), 117 (1985), Aharoni et al, Marcomolecules 15, 1093 (1982), and the following United States Pat. Nos.

| | |
|---|---|
| 4,289,872 | 4,558,120 |
| 4,376,861 | 4,568,737 |
| 4,507,466 | 4,587,329 |
| 4,515,920 | 4,599,400 |
| 4,517,122 | 4,600,535 |

THE INVENTION

This invention, in its presently preferred embodiments, provides a multiple antigen peptide system comprising a dendritic polymer base with a plurality of anchoring sites covalently bound to antigenic molecules which may be the same or different. The polymers comprise a central core molecule having at least two functional groups to which molecular branches having terminal functional groups are covalently bound. The terminal functional groups on the branches are covalently bonded to antigenic molecules. The antigenic molecules are principally described herein as peptide antigens, but they are not limited to peptide antigens or even to antigens.

The selected antigen may be separately synthesized or otherwise obtained and joined to the carrier. Alternatively, the antigen may be synthesized on the carrier. For instance, if the antigen is an oligopeptide or relatively low molecular weight polypeptide, and the available functional groups on the polymer are amino groups or carboxyl groups, the antigen can be synthesized by extending each branch of the polymer utilizing known peptide synthesis techniques.

Figure 1:
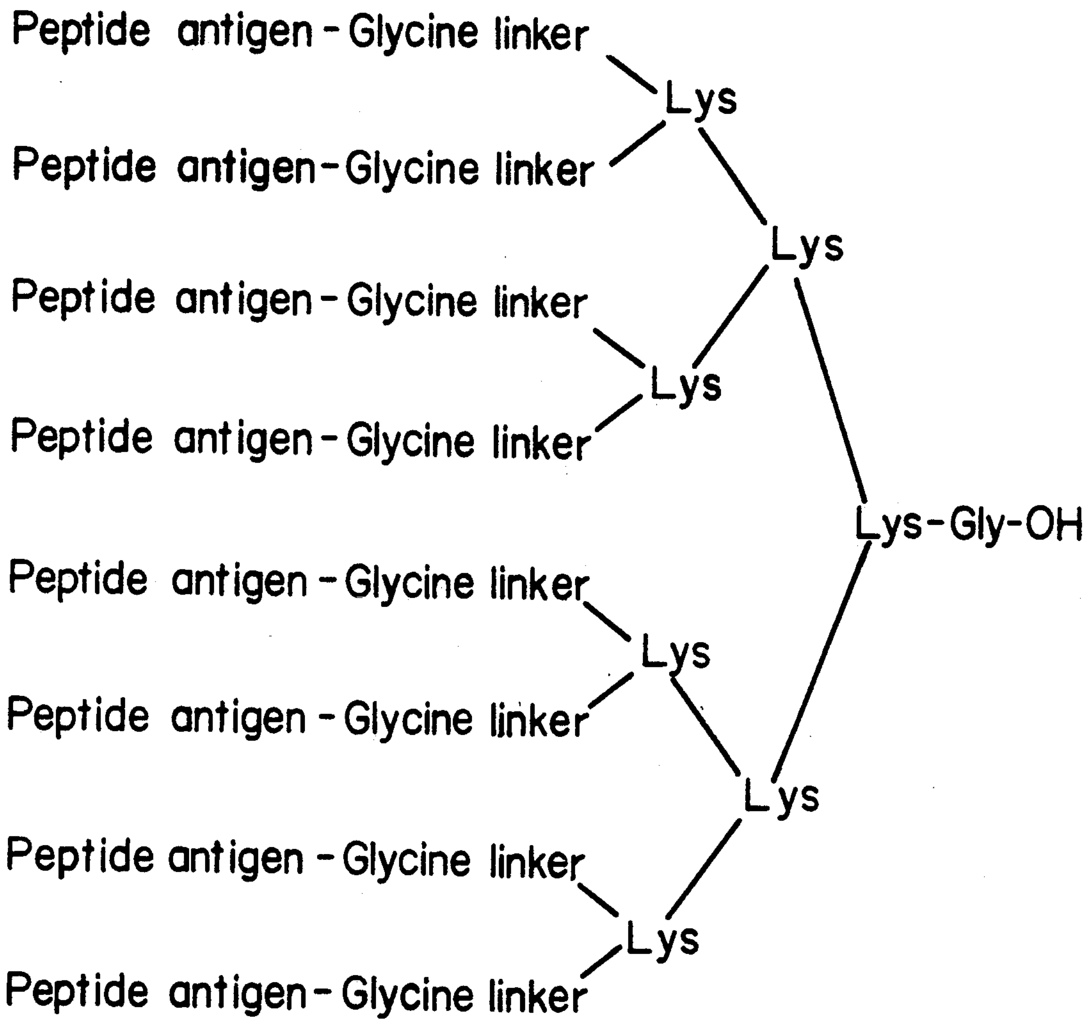
FIG. 1 is a representation of a typical antigen product of the invention in which 8 peptide antigens are linked through glycine linkers to a dendritic lysine substrate.

FIG. 1 shows the structure of a dendritic polymer which may be employed in the practice of this invention. As will be seen, it is a three generation dendritic polylysine product. It may be produced by conventional solid phase techniques by generating the polymer on a Pam or a Pop resin. See Mitchell et al, J. Org. Chem. (1978) 43, 2845 and Tam et al, J. Am. Chem. Soc., (1980) 102 6117. The polymer is then cleaved from the resin using, preferably HF:DMS. The dendritic polylysine, as shown, was built from a glycine linker originally joined through a benzyl linker to the resin. Other linkers such as alanine can be employed. Of course, the linker can be omitted, or a plurality of linker molecules can be utilized.

FIG. 1 shows a peptide antigen joined directly to each of the available functional groups on each terminal lysine moiety. In the case when the antigen is a relatively short peptide, e.g. 6 to 14 residues, it has been observed that it is best to extend the polylysine by a linker such as a simple tri- or tetrapeptide of glycine, alanine or beta alanine. However, for antigenic peptides with more than 14 residues, the linker is normally unnecessary.

This invention has been described for convenience, principally as applied to products built on lysine as the core molecule. In fact lysine and lysine like molecules such as ornithine, nor-lysine and -amino alanine are preferred molecules for building the products of this invention because they are relatively easy to obtain, they are easy to work with and they afford good yields.

Such molecules can be represented by the general formula:

$$H_2N-(CH_2)_x-\underset{\substack{|\\ H}}{\overset{\substack{(CH_2)_y-NH_2\\ |}}{C}}-(CH_2)_z-COOH$$

wherein x, y and z are integers from 0 to 10, preferably 0 to 4 provided that at least one of them is 1 and the amino groups cannot be attached to the same carbon atom. In the most preferred molecules the total of x, y and z is from 2 to 6 and the amino groups are separated by at least two methylene groups.

Other preferred core molecules include ethylene diamine and like molecules with longer chains such as propylene diamine and butylene diamine. Such molecules may be represented by the general formula:

$$H_2N-CH_2-(CH_2)_n-CH_2-NH_2$$

wherein n is an integer from 0 to 10, preferably 0 to 3.

Of course ammonia can also be employed as a core molecule.

The development of synthetic vaccines against a large number of diseases has recently been greatly accelerated because of the recognition that a vaccine need not be based on a native protein, but may be based on a low molecular weight segment of the native protein. These segments, normally called immunogenic determinants or epitopes are capable of stimulating the production of antibodies which will protect against infection by an infectious vector of the native protein antigen. The immunogenic determinants are often low molecular weight peptides which can be conveniently synthesized. If they cannot be synthesized, they may be separated in pure form from the native protein itself. Hereinafter, these antigenic immunostimulants will be referred to as antigenic peptides.

The principal embodiments of this invention may be broadly defined as antigenic products comprising a dendritic core molecule or polymer to which a plurality of antigens such as antigenic peptides are covalently bonded to the available functional groups. The antigens may be the same or different, i.e., they may be antigens associated with one or more diseases or they may be T-cell and B-cell antigens associated with the same disease.

T-helper cell epitopic peptides can be identified, as described above in the references of Sinigaglia et al etc. Briefly, once the amino acid sequence of a protein is known, peptides corresponding to fragments of the protein can be synthesized and injected in mammals. T-cells can then be harvested from blood samples of the immunized mammals and incubated in vitro in the presence of the peptide used for immunization. Such peptides are considered T-helper cell epitopic peptides if the T-cells proliferate during such incubation in the presence of such a peptide. To demonstrate whether these T-cell peptides are T-helper peptides, they are tested for elicitation of antibodies to a B-cell epitope by covalently linking the T-cell and the B-cell epitopic peptide and using the thus formed conjugate for immunization.

More specifically, the principal embodiments of the invention may be defined as antigenic products or carrier systems comprising a dendritic polymer base which is a central core molecule having at least two available functional groups to which branches of selected lengths are joined. Each branch of the molecule terminates with at least one available, anchoring, functional group, a plurality of which are convalently bonded to antigenic molecules.

Some of the antigenic peptides which are currently available either commercially or by known synthetic or isolation techniques are listed in Table 1. The table lists the peptides which are segments of proteins associated with the disease or pathogen identified in the second column. The references identify the publications which describe the peptides and how to obtain them. The conventional abbreviations are used for the amino acids.

TABLE 1

PEPTIDE SEQUENCES SUITABLE FOR DEVELOPMENT OF VACCINES USING MAPS

| Peptide | Pathogen/ Disease (protein) | Ref |
|---|---|---|
| A. H—(ASN—Ala—ASN—Pro)$_n$—OH n > 3 | Malaria, ccs protein of *Plasmodium falciparum* | 1 |
| B. H—(Gly—Asp—Arg—Ala—Asp—Gly—Gln—Pro—Ala)$_n$—OH n > 2 | Malaria, ccs protein of *Plasmodium vivax* | 2 |
| C. Glu—Gln—Asn—Val—Glu—His—Asp—Ala | Malaria, Pf 155 of *Plasmodium falciparum* | 3 |
| D. Asn—Ala—Glu—Asn—Lys—Glu—Glu—Leu—Thr—Ser— | Malaria, Merozoite surface pro- | 4 |

TABLE 1-continued
PEPTIDE SEQUENCES SUITABLE FOR DEVELOPMENT OF VACCINES USING MAPS

| Peptide | Pathogen/ Disease (protein) | Ref |
|---|---|---|
| Ser—Asp—Pro—Glu—Gly—Gln—Ile—Met | tein of Plasmodium falciparum | |
| E. Met—Gln—Trp—Asn—Ser—Thr—Ala—Phe—His—Gln—Thr—Leu—Gln—Asp—Pro—Arg—Val—Arg—Gly—Leu—Tyr—Leu—Tyr—Leu—Pro—Ala—Ala—Gly—Gly | Hepatitis, pre S(1) | 5 |
| F. Asp—Pro—Arg—Val—Arg—Gly—Leu—Tyr—Phe—Pro—Ala—Gly—Gly—Ser—Ser—Ser—Gly—Thr—Val | Hepatitis, pre S(2) | 6 |
| G. Cys—Thr—Lys—Pro—Thr—Asp—Gly—Asn—Cys—Thr—Cys | Hepatitis Surface antigen | 7,8 |
| H. Asn—Phe—Ser—Thr—Ala—Asp—Ser—Ala—Lys—Ile—Lys—Thr—Leu—Glu—Ala—Glu—Lys—Ala—Asp—Leu—Gly—Lys—Ala—Leu—Gly—Ala | Streptococcus pyogenes, M-protein | 9 |
| I. Tyr—Ser—Thr—Leu—Tyr—Arg—Trp—Leu—Asp—Asp—Ser—Phe | Poliovirus, replicase protein | 10 |
| J. Asn—Ala—Pro—Ser—Lys—Thr—Lys—Leu—Glu—Pro—Ser—Ala—Phe | Poliovirus, replicase protein | 10 |
| K. Lys—Lys—Pro—asn—Val—Pro—Thr—Ile—Arg—Thr—Ala—Lys—Val—Gin | Poliovirus, VPg | 11 |
| L. Gly—Ser—Gly—Val—Arg—Gly—Asp—Ser—Gly—Ser—Leu—Ala—Leu—Arg—Val—Ala—Arg—Gln—Leu—Pro | Foot and Mouth Disease VPI | 12 |
| M. Arg—His—Lys—Gln—Lys—Ile—Val—Ala—Pro—Val—Lys—Gln—Thr—Leu | Foot and Mouth Disease VPI | 13 |
| N. Gly—Leu—Phe—Gly—ala—Ile—Ala—Gly—Phe—Ile—Glu | Influenza, HA2 Hemagglutinin protein | 14 |
| O. Arg—Ser—Lys—Ala—Phe—Ser—Asn—Cys—Tyr—Pro—Tyr—Asp—Val—Pro—Asp—Tyr—Ala—Ser | Influenza, Ha1 Hemagglutinin protein | |
| P. Arg—Ile—Leu—Ala—Val—Glu—Arg—Tyr—Leu—Lys—Asp—Gln—Gln—Leu—Leu—Gly—Ile—Trp—Gly—Cys—Ser | HIV-I, envelope glyco-protein of human T-lymphotropic virus type III | 15 |

1 Zavala, et al Science (1985) 228: 1436
2 McCutchan, et al Science (1985) 230: 1381
3 Udomsangpetch, et al Science (1986) 231: 57
4 Ravetch, et al Science (1984) 227: 1593
5 Neurath, et al Science (1984) 224: 392
6 Itoh, et al Proc. Natl. Acad. Sci. USA (1986) 83: 9174
7 Prince, et al Proc. Natl. Acad. Sci. USA (1982) 79: 579
8 Bhatnager, et al Proc. Natl. Acad. Sci. USA (1982) 79: 4400
9 Beachey, et al J. Biol. Chem. (1983) 258: 13250
10 Baron, et al Journal of Visology (1982) 43: 969
11 Baron, et al Cell (1982) 28: 395
12 Bittle, et al Nature (London) (1983) 298: 30
13 Atassi, et al Proc. Natl. Acad. Sci. USA (1982) 80: 840
14 Muller, et al Proc. Natl. Acad. Sci. USA (1982) 79: 569
15 Wang, et al Proc. Natl. Acad. Sci. USA (1986) 83: 6159

Antigens E and F are T-cell antigens associated with hepatitis. Antigen G is a B-cell antigen associated with the same disease. It has been found that when a T-cell and a B-cell antigen to hepatitis are placed on the same MAP substrate the immunoggenic response to a hepatitis virus challenge is unusually strong.

It has been found that these and other antigenic peptides can be joined to dendritic polymers to synthesize products useful for the production of monoclonal antibodies, vaccines and other useful products. The products are, of course, novel.

A particular advantage of this invention is that the dendritic polymer can serve as a carrier for two or more different antigens. This is particularly useful for producing multivalent vaccines, or for producing vaccines against parasites such as the maleria parasite which is pathogenic in any of three different stages. Vaccines produced from antigenic products of the invention in which T-cell antigens and B-cell antigens associated with the same disease are joined to the dendritic polymer in any of the various configurations illustrated in the figures are especially useful because they are capable of generating extremely high antibody titers.

One embodiment of this invention which utilizes this procedure is based on the use of a dendritic polylysine or other structurally similar molecule employing different amino blocking groups, one of which is stable to acid hydrolysis, the other of which is stable to alkaline hydrolysis. This makes it possible to protect either of the amino groups of lysine by the orthogonal protection method.

Fluorenylmethyloxycarbonyl (Fmoc) is a base labile protecting group and is completely stable to acidic deprotection. The t-butoxycarbonyl blocking group (Boc) is stable under basic conditions but not stable under mildly acidic conditions such as 50% trifluoroacetic acid. By choosing Boc-lys (Boc)-OH, Boc-lys (Fmoc)-OH, Fmoc-lys (Boc)-OH or Fmoc-lys (Fmoc)-OH it is possible to place one set of antigens on the alpha amino group of lysine and another on the omega amino group. Those skilled in the art of peptide synthesis can readily devise methods of achieving the same types of products using diverse blocking groups and other dendritic polymers.

A few general observations applicable to the synthesis of MAPS will be of assistance to those skilled in the art. These are:

1. The syntheses generally require a long coupling time (2–4 hours).

2. Dimethyl formamide is generally a more suitable solvent than methylene dichloride.

3. The peptide resin should not be dried at any stage of the synthesis since resolvation is extremely difficult.

4. Coupling should be closely monitored for completion of the coupling by the quantitative ninhydrin method.

5. The MAPS is best cleaved from the resin by the improved acid deprotection method with either HF or TFMSA [Tam, et al J. Am. Chem. Sic. (1983) 105: 6442 and J. Am. Chem. Soc. (1986) 108: 5242] in dimethyl sulfide to avoid strong acid catalyzed side reactions.

6. MAPS tend to strongly aggregate after cleavage from the resin support. Purification is best effected by extensive dialysis under basic and strongly denaturing conditions in a dialysis medium which is 8M in urea and mercaptoethanol to remove undesirable aromatic additives of the cleavage reactions such as p-cresol and thiocresol. Further purification, if desired, can be effected using high performance gel-permeation or ion exchange chromotography. In most cases the MAPS could be used directly without further purification.

It will be apparent to those skilled in the art that many variations of the structures shown and discussed herein are possible. All such variations are specifically included within the scope of this invention. For example, referring to FIG. 1, the glycine at the root of the dendritic polymer, i.e., the free glycine could be joined to, or replaced with, a peptide antigen which may be the same or different from the other peptide antigens on the branches of the dendritic polymer molecule. The peptide antigens themselves may serve as the residue to which other lysine or similar molecules may be attached to provide additional branches to which still additional peptide antigens, antibiotics or non-peptide antigens may be attached.

Figure 8A:
FIGS. 8A–8L show possible configurations of the products of the invention with the same or different antigens in a dendritic polymer.
Figure 8B:
Figure 8C:
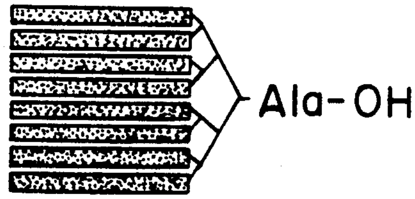
Figure 8D:
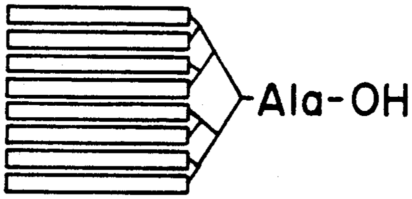
Figure 8E:
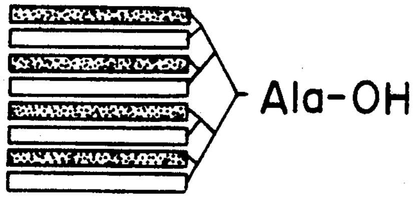
Figure 8F:
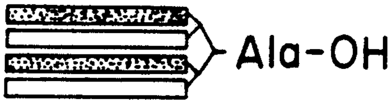
Figure 8G:
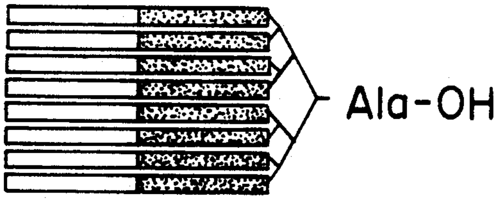
Figure 8H:
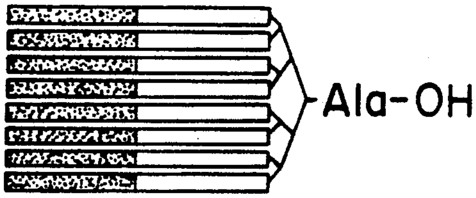
Figure 8I:
Figure 8J:
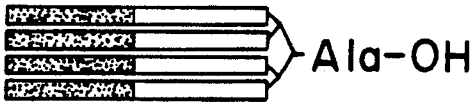
Figure 8K:
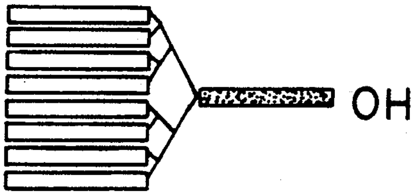
Figure 8L:
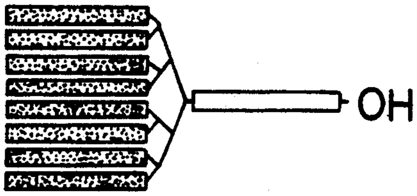
Figures 9A, 9B, 9C, 9D, 9E:
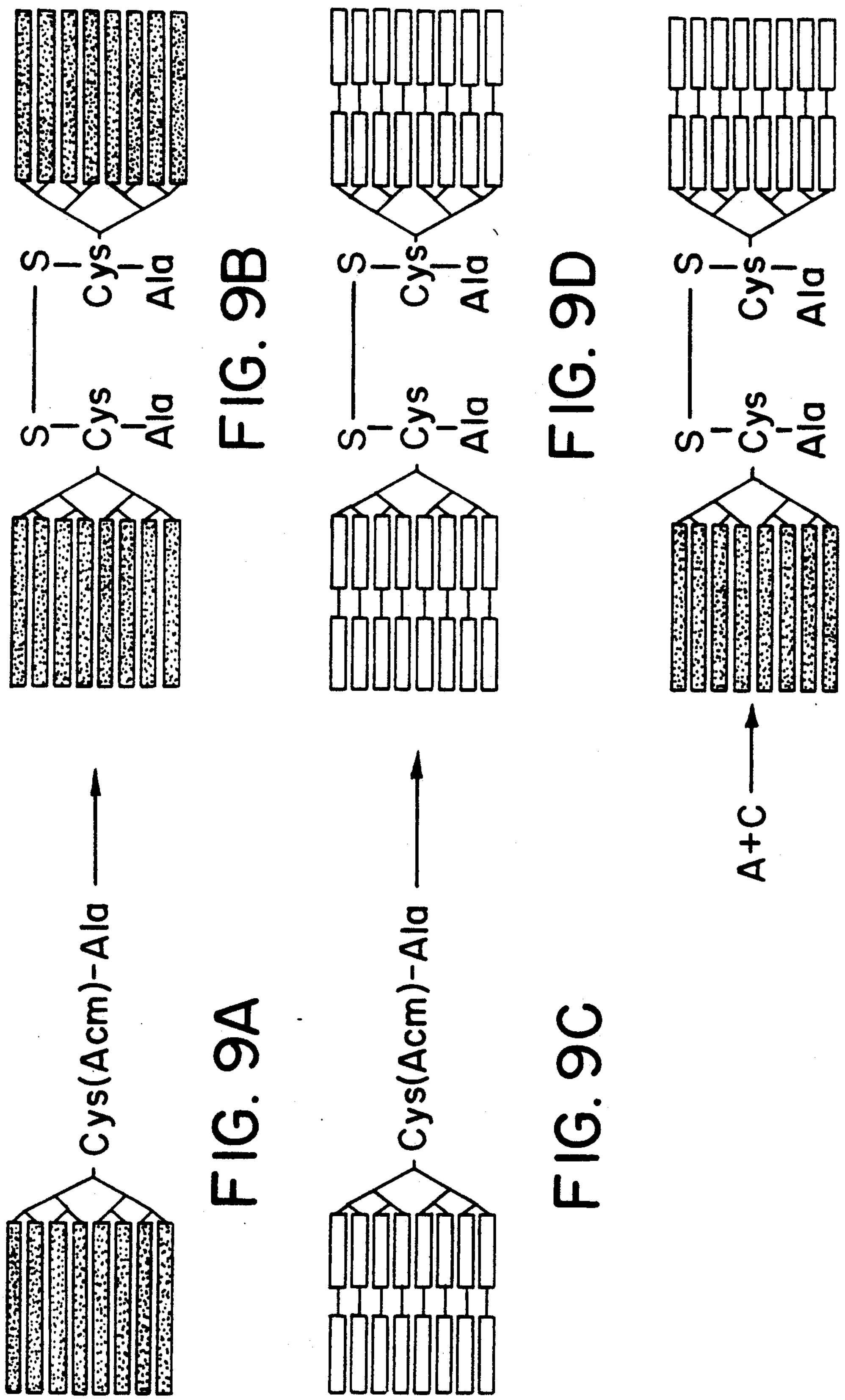
FIGS. 9A–9E and 10A–10B are illustrations of the formation of antigenic products in which a disulfide bridge joins 2 dendritic polymers.

FIGS. 8 and 9 illustrate other possible configurations of the products of this invention with the same or different antigens on a dendritic polymer base. In the figures, the solid blocks represent different antigens which, as aforesaid may be antigens to different diseases such as influenza and measles or T-cell and B-cell antigens to the same disease, for example hepatitis.

FIGS. 8A and 8B represent two different monoantigenic MAP products in which one antigen is joined to a dendritic polymer with four branches.

FIGS. 8C and 8D are similar to 8A and 8B except that the dendritic polymer carrier has eight branches.

FIG. 8E represents an eight branch dendritic polymer base with alternating antigens. FIG. 8F is similar except that the polymer base has only four branches. Such products may be synthesized by the procedure described above in which one amino group with a base stable blocking group while extending one branch of the polymer chain and then blocking the extended chain with an acid stable group and extending the other branch after removing the base stable group.

FIGS. 8G through 8J represent MAP structures in which there is a tandem arrangement of different antigens on eight and four branched substrates respectively.

FIGS. 8K and 8L represent somewhat different structures which are still within the scope of the invention. In these structures, one antigen is joined to the root of the dendritic polymer and another is joined to the branches.

FIG. 9 illustrates the formation of monoantigenic and diantigenic products in which two antigenic dendritic polymers are joined through a disulfide bridge.

Figures 10A, 10B:
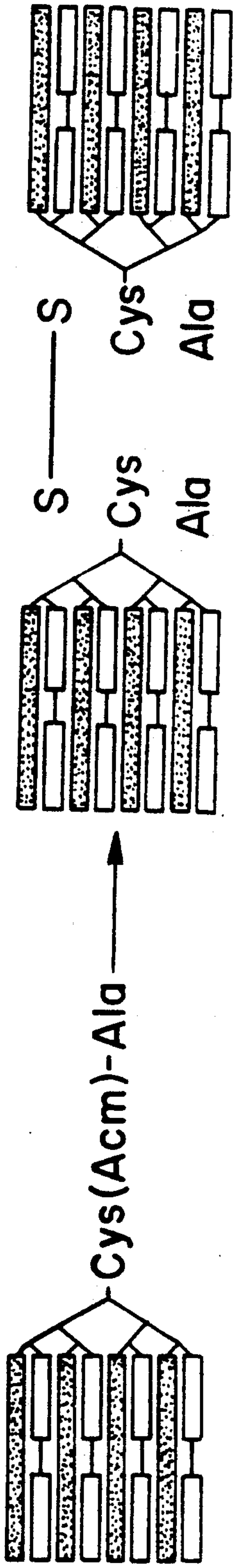

FIG. 10 illustrates a similar structure in which the disulfide bridge joins diantigenic dendritic polymers in which the antigens are arranged in alternate configurations.

The products of this invention can be employed to produce vaccines using any of the procedures known to those skilled in the art. The products can, for example, be suspended in inert oil, suitably a vegetable oil such as sesame, peanut or olive oil. Alternatively they can be suspended in an aqueous isotonic buffer solution at a pH of about 5.6 to 7.4. Typically, such solutions will be made isotonic with sodium chloride and buffered with sodium citrate-citric acid or with phosphate. The solutions may be thickened with a thickening agent such as methyl cellulose.

Vaccines may also be prepared in emulsified form, either water in oil or oil in water. Any of a wide variety of pharmaceutically acceptable emulsifying agents may be employed including, for example acacia powder or an alkaryl polyether alcohol, sulfonate or sulfate such as a Triton.

Stabilizers such as sorbitol or hydrolyzed gelatin may also be added to any of the above described compositions. It is not unusual to incorporate an antibiotic such as neomycin or other antiinfective agent to prevent infection.

Because the products of this invention provide a high concentration of antigen in a small molecular volume, in many instances the vaccines of the invention will be employed without adjuvants. However, if an adjuvant is employed it may be selected from any of those normally employed to stimulate the immunogenic systems of mammals. These include, for example, Freund's adjuvant (complete or incomplete), Adjuvant 65 (containing peanut oil, mannide monooleate and aluminum monostearate), and mineral gels such as aluminum phosphate or alum. Freund's adjuvant is no longer used in vaccine formulations for humans or for food animals because it contains nonmetabolizable mineral oil and is a potential carcinogen. It can be used in vaccines for non-food animals. Mineral gels are widely used in commercial veterinary vaccines.

The vaccines of the invention may be defined as comprising a pharmaceutically acceptable carrier, of the general nature described above, together with an amount of an antigenic product of the invention which is sufficient to produce an immunological response. An effective amount may be very small. It will, as is known, vary with the antigen. With the products of this invention, because of the high concentration of antigen in a low molecular volume, it will be lower than with ordinary vaccines employing the same antigens. The quantity which constitutes an effective amount may vary depending on whether the vaccine is intended as a first treatment or as a booster treatment.

It may be convenient to provide the products of this invention as lyophilized or freeze dried powders ready to be reconstituted with a pharmaceutically acceptable carrier just prior to use.

This invention has been described principally as it is applied to the production of vaccines based on peptide type antigens. However, as will be apparent to those skilled in the art, it is not limited to such products. For example, the core molecule could be used as a carrier for an antibiotic, a vitamin, an antidiabetic, a steroid, a cardiovascular agent or other physiologically active agent. It could support a diagnostic agent. Additionally, the core molecule could support a structure other than a polyamide, and the antigen need not necessarily be a peptide. The covalent bond which joins the antigen or other supported moiety to the carrier may be an ester, ether, urethane or some other type of covalent linkage.

The products of the invention may be employed in various diagnostic tests including radioimmunoassay, precipitation, complement fixation, direct and indirect immunofluorescence, agglutination and enzyme linked immunoassay. For such testing the diagnostic moiety joined to the dendritic polymer may be labeled with a detectable label, or it may be caused to react with a labeled product such as a labeled antibody to product a detectable reaction product. Useful labels include fluorescent labels such as fluorescein, rhodamine or auramine. Radioisotopes such as $^{14}C$, $^{131}I$, $^{125}I$ and $^{35}S$ may be employed. Enzyme labels which may be utilized include, for example, horse radish peroxidase, $\beta$-D-glucosidase, $\beta$-D-galactosidase, urease, glucose oxdase plus peroxidase, and acid phosphatase. Methods for labeling are well known and need not be described.

A typically useful diagnostic product within the scope of this invention can be produced by supporting the 21-segment peptide identified by the notation P in Table 1. This product can be utilized in lieu of the whole HTLV-III virus. This is the virus associated with the acquired immune deficiency syndrome, AIDS. Use of the product of this invention in, for example an enzyme linked immunoassay procedure will eliminate false positives which arise due to impurities which may be present in the whole virus preparation.

The following examples are given by way of illustration only and should not be considered limitations of this invention many apparent variations of which are possible without departing from the spirit and scope thereof. The following abbreviations are used in the examples:

Boc-13 t-butoxycarbonyl
TFA—trifluoracetic acid
DMF—dimethylformamide
DCC—dicyclohexylcarbodiimide
Tos—tosyl
Bzl—benzyl
Dnp—dinitrophenyl
2ClZ—2-chlorocarbobenzoxy
DIEA—diisopropoylethylamine
TFMSA—trifluormethylsulfonic
BSA—bovine serum albumin
HPLC—high performance liquid chromatography
TBR—tumor bearing rabbit
ATP—adenosine triphosphate
Dnp—dinitrophenyl.
ClZ—chlorobenzyloxycarbonyl
BrZ—bromobenzyloxycarbonyl
ELISA—enzyme linked immunoabsorbent assay

EXAMPLE 1

General Methods for the Synthesis of Multiple-Antigen Peptides

The synthesis of an octabranched matrix core with peptide antigen was carried out manually by a stepwise solid-phase procedure [Merrifield, R. B. J. Am. Chem. Soc. (1963) 85, 2149] on Boc-$\beta$Ala-$OCH_2$-Pam resin with a typical scale of 0.5 g of resin (0.05 mmol and a resin substitution level of 0.1 mmol/g for the present synthesis but was somewhat lower when a higher branching of core lysinlyl matrix was used). After the removal of the Boc-group by 50% TFA and neutralization of the resulting salt by DIEA, the synthesis of the first level of the carrier-core was achieved using 4 molar excess of preformed symmetrical anhydride of Boc-Lys(Boc) (0.2 mmol) in DMF and was then recoupled via DCC alone in $CH_2Cl_2$. The second and third level were synthesized by the same protocol with 0.4 and 0.8 mmol respectively of preactivated Boc-Lys(-Boc) to give the octabranching Boc-Lys(Boc)-core matrix. However, all subsequent couplings of the peptide-antigen sequence require 1.6 mmol of preactivated amino acids. The protecting groups for the synthesis of the peptide antigens were as follows: Boc group for the $\alpha$-amino terminus and benzyl alcohol derivatives for most side chains of trifunctional amino acids i.e., Arg-(Tos), Asp(OBzl), Glu(OBzl), His(Dnp), Lys(2ClZ), Ser(Bzl), Thr(Bzl), and Tyr(BrZ). Because of the geometric increase in weight gain and volume, a new volume ratio of 30 ml of solvent per g of resin was used. Deprotection by TFA (20 min) was preceded by two TFA prewashes for 2 min each. Neutralization by DIEA was in $CH_2Cl_2$ (5% DIEA) and there was an additional neutralization in DMF (2% DIEA). For all residues except Arg, Asn, Gln, and Gly, the first coupling was done with the preformed symmetric anhydride in $CH_2Cl_2$ and a second coupling was performed in DMF; each coupline was for 2 h. The coupling of Boc-Asn and Boc-Gly were mediated by the performed 1-hydroxybenzotriazole ester in DMF. Boc-Gly and Boc-Arg were coupled with DCC alone to avoid the risk of formation of dipeptide and lactam formation, respectively. All couplings were monitored by a quantitative ninhydrin test [Sarin, V. K., et al Anal. Biochem. (1981) 117, 147] after each cycle, and if needed, a third coupling of symmetrical anhydride in DMF at 50° for 2 h was used [Tam, J. P. (1985) In "Proc. am. Pept. Sympo., 9th"(c. M. Deber, K. D. Kopple and V. J.]. The synthesis was terminated with acetylation in acetic anhydride/DMF (3 mmol) containing 0.3 mmol of N,N-dimethylpyridine.

After completion of the MAPS, protected peptide-resin (0.3 g) was treated with 1M thiophenol in DMF for 8 h (3 times and at 50° C. if necessary to complete the reaction) to remove the $N^{im}$-dinitrophenyl protecting group of His (when present), with 50% TFA/$CH_2Cl_2$ (10 ml) for 5 min to remove the $N^{\alpha}$-Boc group, and with the low/high-HF method [Tam, J. P., Heath, W. F. & Merrifield, R. B. J. Am. Chem. Soc. (1983) 105, 6442] or the low-high TFMSA method [Tam, J. P. Heath, W. F. & Merrifield, R. B. J. Am. Chem. Soc. (1986) 108, 5242] of cleavage to give the crude MAPS. The crude peptide was then washed with cold ether mercaptoethanol (99:1, v/v, 30 ml) to remove p-thiocresol and p-cresol and extracted into 100 ml of 8M urea, 0.2M dithiothreitol in 0.1M Tris buffer, pH 8.0. To remove all the remaining aromatic by-products generated in the cleavage step, the peptide in the dialysis tubing (Spectra Por 6,M.W. cutoff 1,000) was equilibrated in a deaerated and $N_2$-purged solution containing 8M urea, 0.1M $NH_4HCO_3$—$(NH_4)_2CO_3$, pH 8.0 with 0.1M mercaptoethanol at 0° C. for 24 h. The dialysis was then continued in 8M, and then in 2M urea, all in 0.1M $NH_4HCO_3$—$(NH_4)_2CO_3$ buffer, pH 8.0 for 12 h and then sequentially in $H_2O$ and 1M HOAc to remove all the urea. The lyophilized MAPS was then purified batchwise by high performance gel-permeation or ion-exchange chromatography. All of the purified material gave a satisfactory amino acid analysis.

EXAMPLE 2

Synthesis and Purification of (Asn-Ala-Asn-Pro)$_8$-MAP (NP-16 MAP), a Peptide Derived from the Sporozoite Stage of *Plasmodium falciparum*

The peptide, (Asn-Ala-Asn-Pro)$_8$-Lys$_4$-Lys$_2$-Lys-OH was synthesized by the general procedure described in Example 1.

The synthesis was initiated with Box-Lys(Boc)-$OCH_2$-Pam-resin (a copoly(styrene-1%-divinylbenzene resin) at a substitution of 0.11 mmol/g of resin. The substitution was found to be 0.88 mmol/g after the sequential addition of three levels of Boc-Lys(Boc) to give an octabranching structure of [Boc-Lys(Boc)$_4$] [Lys(Boc)$_2$-Lys(Boc)-$OCH_2$-Pam resin. The synthesis continued with 2.5 g of resin in a modified Beckmann 990 synthesizer (Beckman Instruments, Palo Alto, Calif.). Synthesis was performed using a computer program that optimized all of the coupling steps. For example, the coupling of Boc-Ala and Boc-Pro were mediated by the symmetric anhydride method in a solvent ratio of $CH_2Cl_2$:dimethylformamide (1:3, v/v) to minimize aggregation and incomplete coupling. The coupling of Boc-Asn was by the performed 1-hydroxybenzotriazole active ester in the same solvent. Each amino acid underwent a double coupling protocol to maximize the coupling yield and essentially bring the reaction to >99.6% completion.

The protected peptide-resin was deprotected in portions. The initial deprotection was carried out with 1.57 g of dried peptide-resin in a reaction vessel and underwent the following procedure to remove the Boc-protecting group and other extraneous materials $CH_2Cl_2$ (3×1 min wash); $CF_3CO_2H$—$CH_2Cl_2$(1:1, 3×2 min) and $CF_3CO_2H$ (3×2 min wash) and then a cleavage reaction containing the following deprotecting reagents: trifluoromethanesulfonic acid:trifluoroacetic acid:tetrahydrothiophene: m-cresol (4:20:12:4, in ml) at 4° C. for 3.5 h. The peptide released by the acidolytic cleavage of the sulfide-assisted cleavage procedure was collected and precipitated by ethl ether (230 ml) pre-chilled to −30° C. The precipitate was centrifuged to a pellet and the ethyl ether was removed in vacuo. The peptide was then dissolved in 0.01M HOAc and dialyzed in 12 liters of 0.01M HOAc. The peptide was then lyophilized to dryness to obtain 60 mg of $(Asn-Ala-Asn-Pro)_8$0MAP. Hydrolysis of the resulting resin after cleavage showed that about 90% of the peptide had been cleaved from the resin support. The low yield was due to incomplete precipitation of the peptide by the ether. The same peptide-resin (1.0 g) was also cleaved by HF:anisole (9:1, v/v total 10ml) at 0° C. for 1 h to give 220 mg of MAP after extensive extraction with 10 to 100% HOAc and a crude yield of 33%. The dialysis was carried out with 10% OHAc.

The peptide after dialysis was then analyzed first by amino acid analysis (after hydrolysis by 6N HCl). The molar ratio of the MAP found was Asn:Ala;Pro;Lys: 1.97 (2): 1.03 (1):1 (1):0.26(0.22) which was in agreement with those expected theoretical values shown in parenthesis. This peptide is referred to as NP-16 MAP.

EXAMPLE 3

Immunization with NP-16 MAP

Inbred 6- to 8-week old mice (C57 Black/6J) were immunized in the footpad with 80 g of NP-16 MAP in complete Freund's adjuvant (1:1) on day 0, and again in incomplete Freund's adjuvant 3 weeks later, and bled a week after the last boosting. The antisera were used without purification.

EXAMPLE 4

Radioimmunoassay of NP-16 MAP

Flexible polyvinylchloride microtiter plates (Falcon Laboratories) were incubated with either NA-16 MAP or with serum albumin conjugated linear peptide of NP-16. After washing several times with PBS, pH 7.4 and incubated overnight with 150 microliters of PBS containing 1% BSA and 0.5M ethanolamine at pH 7.5 (PBS-BSA-Eth buffer), 30 microliters of murine antisera was placed in each well. After incubation for one hour at room temperature, each well was washed three times with PBS-BSA-Eth containing 0.5% Tween-20 (ICI Americas Inc., Wilmington, Del.) to eliminate unbound material. Thirty microliters (about $4\times10^4$ counts per minute) of $^{125}$I-labeled, affinity-purified goat anti-mouse immunoglobulin were placed in each well to label the bound antisera. The wells were washed, cut and counted. The results of the radioimmunoassays are shown in FIG. 2.

Figure 2:
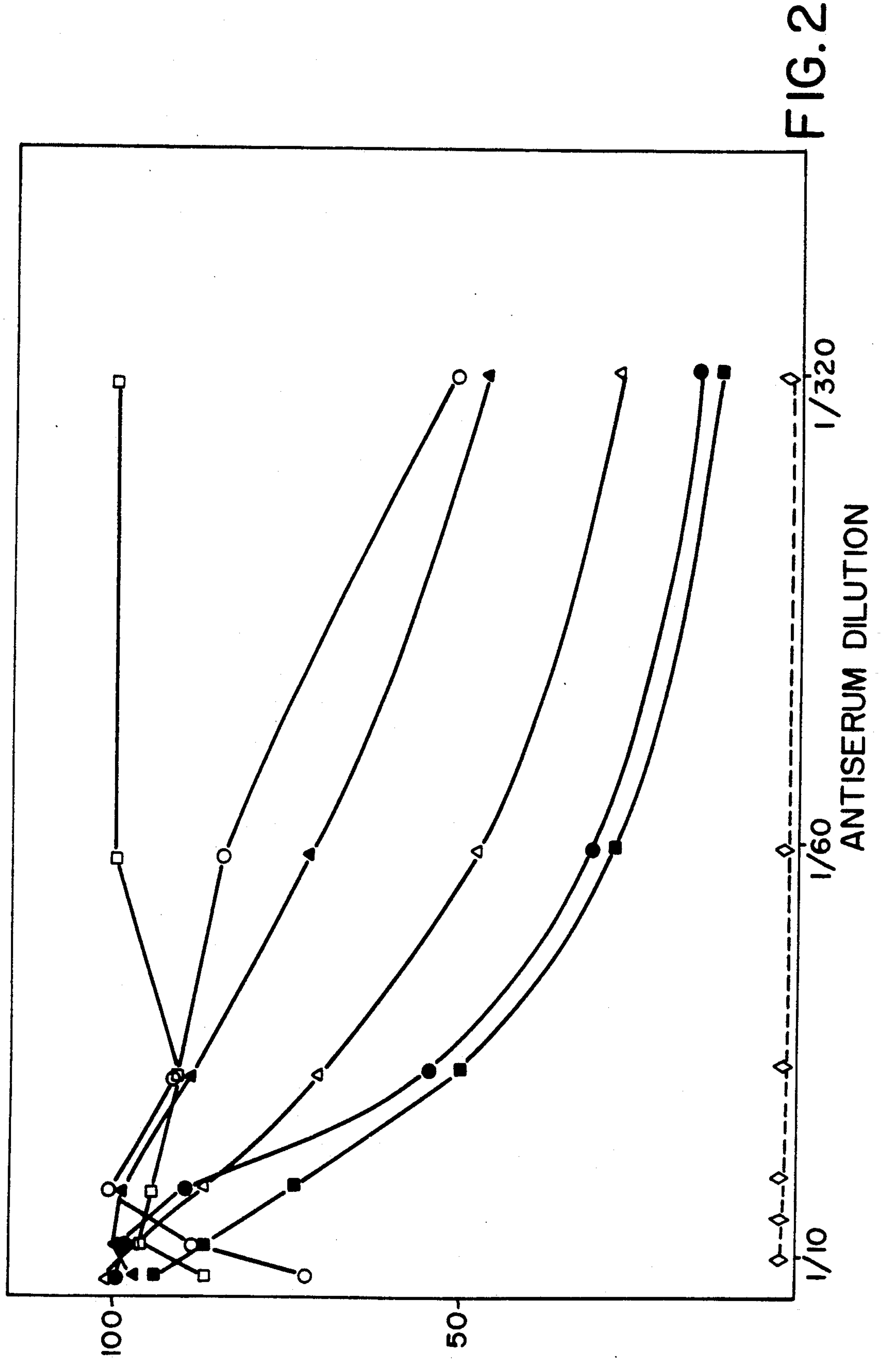
FIG. 2 is an illustration of antibody titers of 6 mice immunized with 80 micrograms of antigen NP-16 MAP in complete Freund's adjuvant.

In FIG. 2, antibody titers between 300 and 1,000 were found in six mice immunized with 80 microgram of antigen (NP-16 MAP) in complete Freunds adjuvant. The titer of each mouse is represented by white and black squares, circles and triangles. A control assay using pre-immune serum gave negative results (about 30–50 cpm above background). Furthermore, immunization with the linear peptide, Asn-Ala-Asn-Pro in tandem four times, did not give the immunological responses and its antisera titer is shown as the black diamond in FIG. 2.

EXAMPLE 5

Synthesis and Purification of Ile-Glu-Asp-Asn-Glu-Tyr-Thr-Ala-Arg-Gln-Gly-MAP (IG-11 MAP), a Peptide derived from the Oncogene Product of Rous Sarcoma Virus The peptide, $(Ile-Glu-Asp-Asn-Glu-Tyr-Thr-Ala-Arg-Gln-Gly)_8-Lys_4-Lys_2-Lys-Gly-OH$, was synthesized by the solid-phase method as generally outlined in Example 1.

The synthesis was initiated on a $Boc-Gly-OCH_2$-Pam-resin (0.12 mmol/g) and sequentially coupled with three levels of Boc-Lys(Boc) to give an octabranching MAP structure and a substitution level of 0.7 mmol/g. The synthesis was carried manually by the methodology and procedure described in Examples 1 and 2. The protecting groups used were as follows: Glu(OBzl), Asp(OBzl), Tyr(BrZ), Thr(Bzl) and Arg(Tos). The peptide resin was cleaved in portions (500 mg each) in the low-high HF procedure as follows: The peptide resin was first treated with the low-HF procedure at 0° C. for 2 h in a HF-apparatus with Teflon-based reaction vessels and HF-dispensing lines containing the following reagents: HF:dimethylsulfide:p-cresol:65:25:10 (v/v, in 10 ml). The HF and dimethylsulfide was rapidly evaporated at 0° C. and the reaction vessel was filled again with 14 ml of HF and the cleavage reaction continued for another hour. After the removal of HF in vacuo, the aromatic scavenger, p-cresol was extracted with ethyl ether, and the peptide-MAP was extracted into 100 ml of 0.1M ammonium bicarbonate and carbonate mixture (pH 8.0). The peptide-MAP was then extensively dialyzed (M.W. cutoff 3,500) in the same ammonium bicarbonate and carbonate mixture, and then in water. Back hydrolysis of the resulting resin showed that the cleavage yield was 94.5% and 335.7 mg of MAP was obtained (78% yield) from the cleavage of 1 g. of resin.

The uncorrected amino acid hydrolysis showed the following molar ratio (with the expected value in parenthesis): Ile, 0.71(1); Glu, 2.96(3); Asp, 1.79(2); Tyr 0.69(1); Thr, 0.9(1); Asm 1(1); Arg, 1.52(1); Gly, 2.45(1.13) and Lys 1.83(0.9). The extraordinary high Gly and Lys molar ratio showed that a termination reaction had occurred or that a poor-solvation led to partial collapse of the resin-matrix. However, C-18 reverse phase HPLC (Vydac, 5 micron, 4.6 mm×250 mm) in 0.01M ammonium bicarbonate and acetonitrile buffer showed the presence of a single major peak at 8.96 min when eluting with a flow rate of 1.5 ml/min and a linear gradient of acetonitrile (3% of acetonitrile/min). the peptide was purified batchwise in this procedure. This peptide is referred to as IG-11 MAP.

EXAMPLE 6

Immunization with IG-11 MAP

Rabbits (New Zealand white, 2,5 Kg) were injected in the hind foot intramuscularly with a total of 1 ml of the IG-11 MAP (1 mg) emulsified in Freund's complete adjuvant (1 ml), two booster injections of the same dose was given subcutaneously three weeks later but in incomplete Freund's adjuvant. The rabbits were bled two weeks after the last injection.

EXAMPLE 7

ELISA of IG-11 MAP

ELISA was used to test all antisera for their ability to react with the IG-11 MAP used for immunization. Peptide antigen (0.5 $\mu$g per well) in carbonate-bicarbonate buffer (pH 9.0) was incubated at 4° C. overnight in a 96-well microtiter plate. Rabbit antisera (serially diluted in 0.01M phosphate-buffered saline) was then incubated with the antigen for 2 h at room temperature. Goat anti-rabbit IgG horseradish peroxidase conjugate was then added and incubated for an additional hour. The bound conjugate was reacted with chromogen (ortho-dianisidine dihydrochloride at 1 mg/ml in 0.01M phosphate buffer, pH 5.95) for 0.5 h and the absorbance of each well was determined with a micro-ELISA reader.

Figure 3:
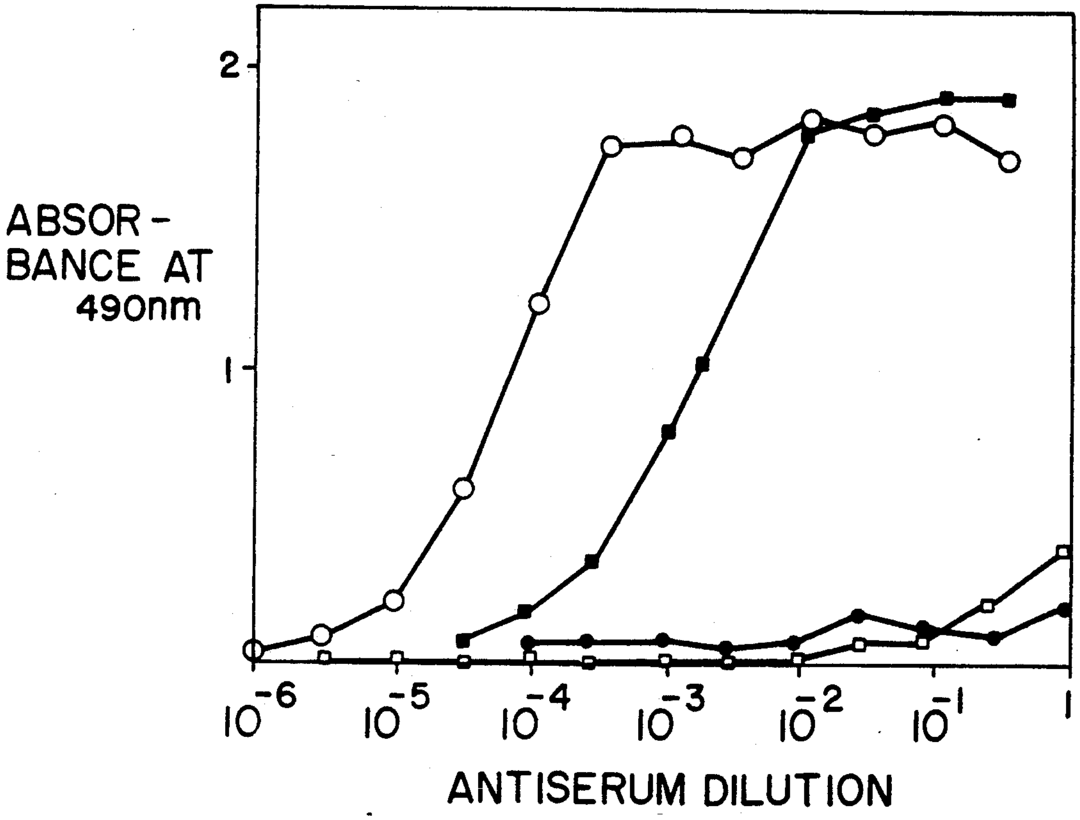
FIG. 3 is an illustration of antibody titers of 2 rabbits immunized with 1 microgram of antigen IG-11 MAP in complete Freund's adjuvant.

The results of the ELISA are shown in FIG. 3.

In FIG. 3, antibody titers between 500 and 3,000 were found in two rabbits immunized with 1 mg of antigen IG-11MAP in complete Freund's adjuvant (single dose). This is represented by the black squares. After a single boosting in incomplete Freund's adjuvant, the antibody titer increased to 20,000 and is represented by white circles. The control preimmune antisera represented by white squares did not show reactivity to the NP-11 MAP antigen. Furthermore, the specificity of the IG-11 MAP antisera could be observed if there was inhibition when the antisera was incubated with a large excess of a linear peptide of IG-11 prepared independently with the MAP. This result is represented as black circles in FIG. 3 and complete inhibition of the immunoreactivity of the antisera of IG-11 MAP to its antigen is observed.

EXAMPLE 8

Immunoprecipitation of the Cognate Protein Sequence of IG-11: The Oncogene Product of Rous Sarcoma Virus The cognate protein sequence of IG-11 is a protein known as $p60^{src}$, a phosphoprotein that has tyrosine kinase activity. To determine that the antisera obtained from IG-11 MAP could recognize and immunoreact with this protein, it was mixed with a cell-extract from chick embryo fibroblast (CEF) culture metabolically labeled with $^{35}$S-methionine. The radiolabeled amino acid enables easy identification of the immunoprecipitate by sodium dodecylsulfate polyacryamide gel electrophoresis analysis (SDS-PAGE). The results are shown in FIG. 4.

Figure 4:
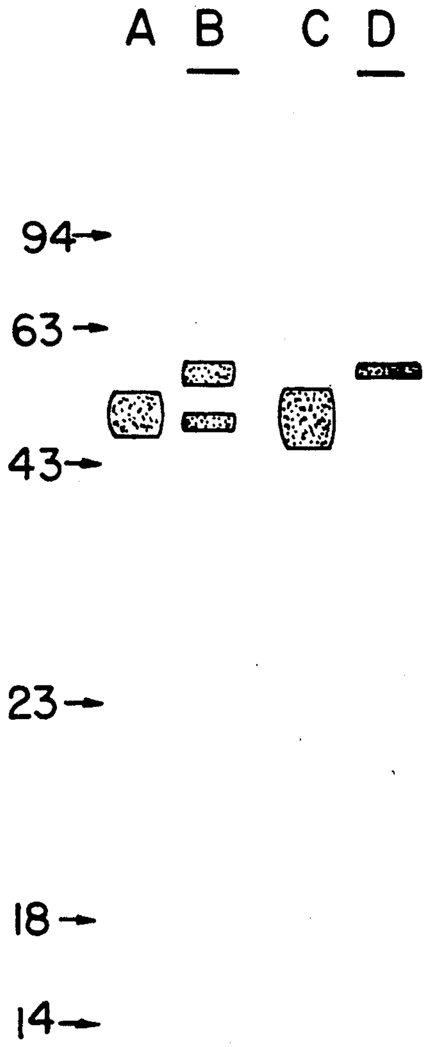
FIG. 4 is an illustration of an SDS-PAGE identification of $p60^{Src}$ labelled with $^{35}S$-methionine.

In FIG. 4, lane 1 and 2 of the SDS-PAGE show an antiserum obtained from tumor-bearing rabbit (infected with Rous sarcoma vius, TBR-serum) and known to immunoreact with $p60^{src}$. Lane 1 (a) shows that the heavy chain of the TBR serum is phosphorylated by labeled ATP to give a characteristic band at about 48 Kd. Lane 2 (B) shows that the TBR-serum precipitated the protein $p60^{src}$ at the molecular weight marker of 60 Kd. Lane 3 (C) shows the IG-11 MAP antiserum at a dilution of 400 produces the same effect as TBR-serum and is being phosphorylated in by labeled ATP as in lane 1. Lane 4 (D) shows that the IG-11 MAP antiserum also precipitates the cognate protein, $p60^{src}$, and gives the characteristic band at 60 Kd.

EXAMPLE 9

Synthesis and Purification of Tyr-Ile-Gln-His-Lys-Leu-Gln-Glu-Ile-Arg-His-Ser-Pro-MAP (YP-13MAP), a Peptide derived from the Oncogene Product of Fujinami Sarcoma Virus The synthesis of this peptide more precisely defined as (Tyr-Ile-Gln-His-Lys-Leu-Gln-Glu-Ile-Arg-His-Ser-Pro)$_8$Lys$_4$-Lys$_2$-Lys-Gly-OH was similar to the peptide-MAP described in Example 5. The synthesis was initiated on a Boc-Gly-OCH$_2$-Pam-resin (0.12 mmol/g) and the synthesis was on an octabranching MAP structure as those described in Example 5. The protecting groups used were as follows: Tyr(BrZ), His(DnP), Lys(ClZ), Glu(OBzl), Arg(Tos) and Ser(Bzl). The peptide-resin (1.0 g) was treated three times with 1.0M thiophenol in dimethylformamide for 2 h to remove the imidazole-dinitrophenyl protecting group. After the removal of the N -Boc protecting group by trifluoroacetic acid, the peptide-resin (0.15 g) was treated with the low-TFMSA procedure using TFMSA:TFA:DMS:m-cresol: 10:50:30:10 (v/v, in 3 ml) at ambient temperature for 4 hours and the resin was washed once with TFA (3 ml). The combined acidic filtrates were cooled to −30° C. and ethyl ether was added to obtain a precipitate. The precipitate, the YP-13 MAP with the Arg(Tos) remained to be converted to Arg, was then subjected to a high TFMSA step with TFSMA:TFA:m-cresol:5:85:10 (v/v) for 1 h. The peptide was precipitated and worked-up as described in the low-TFMSA step and subjected to dialysis as described in Example 5.

The cleavage yield based on the acid hydrolysis of the resulting resin was 85%. Amino acid hydrolysis of the crude YP-13 MAP showed satisfactory molar ratio of the expected values. The peptide YP-13 MAP was purified in high performance gel permeation system (Zorbax, Bio-series, 9.4×250 mm, DuPont Instruments, Wilmington, Del.) in 0.2M Na$_2$HPO$_4$, pH 7.0, at a flow rate of 1.0 ml/min.

EXAMPLE 10

Immunization with YP-13 MAP

Two rabbits (New Zealand white, 2.5 Kg.) were immunized by subcutaneous injections of YP-13 MAP (1 mg in phosphate buffer saline) in complete Freund's adjuvant (1:1) on day 0 and again in incomplete Freund's adjuvant (1:1) on days 21 and 42, and were bled on day 49.

EXAMPLE 11

ELISA of YP-13 MAP

Figure 5:
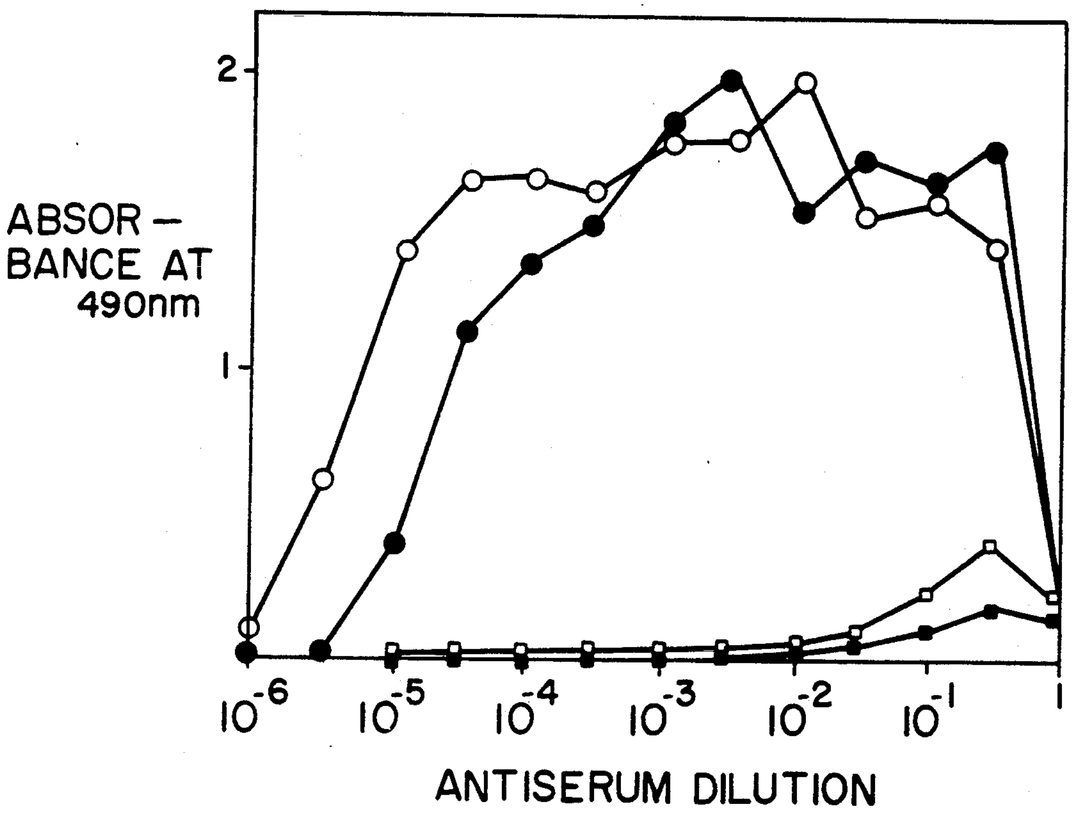
FIG. 5 is an illustration of antibody tiers of 2 rabbits immunized with 1 microgram of antigen YP-13 MAP in complete Freund's adjuvant.

The immunological response to YP-13 MAP was measured by ELISA as described in Example 7. The results of the ELISA are shown in FIG. 5. In FIG. 5, antibody titers between 1,000 to 10,000 were found in two rabbits with 1 mg of antigen YP-13 MAP in complete Freund's adjuvant (single dose). This is represented by the black circles. After two boosting in incomplete Freunds adjuvant, the antibody titer increased to about 50,000 and is represented by white circles. The control preimmune antisera represented by black squares did not show reactivity to YP-13 MAP and furthermore the YP-13 MAP antisera did not show any cross-reactivity with other MAP antigen such as IG-11

MAP (see Example 5–7). This is represented as white squares.

EXAMPLE 12

Synthesis and Purification of Phe-Glu-Pro-Ser-Glu Ala-Glu-Ile-Ser-His-Thr-Gln-Lys-Ala-MAP (FA 14MAP), a Peptide derived from the β-Chain of T-cell Receptor The synthesis and purification of FA-14 MAP more precisely defined as (Phe-Glu-Pro-Ser-Glu-Ala-Glu-Ile-Ser-His-Thr-Gln-Lys-Ala)$_8$-Lys$_4$-Lys$_2$-Lys-Gly-OH was according to the Example 1. The peptide was dialyzed and used as an immunogen without further purification.

EXAMPLE 13

Immunization with FA-14 MAP

Mice (Balb/c) were immunized with FA-14 MAP (80 μg) in complete Freund's adjuvant or with Alum. The mice were boostered after one month and bled one week after the second immunization.

EXAMPLE 14

Indirect ELISA of FA-14 MAP

Figure 6:
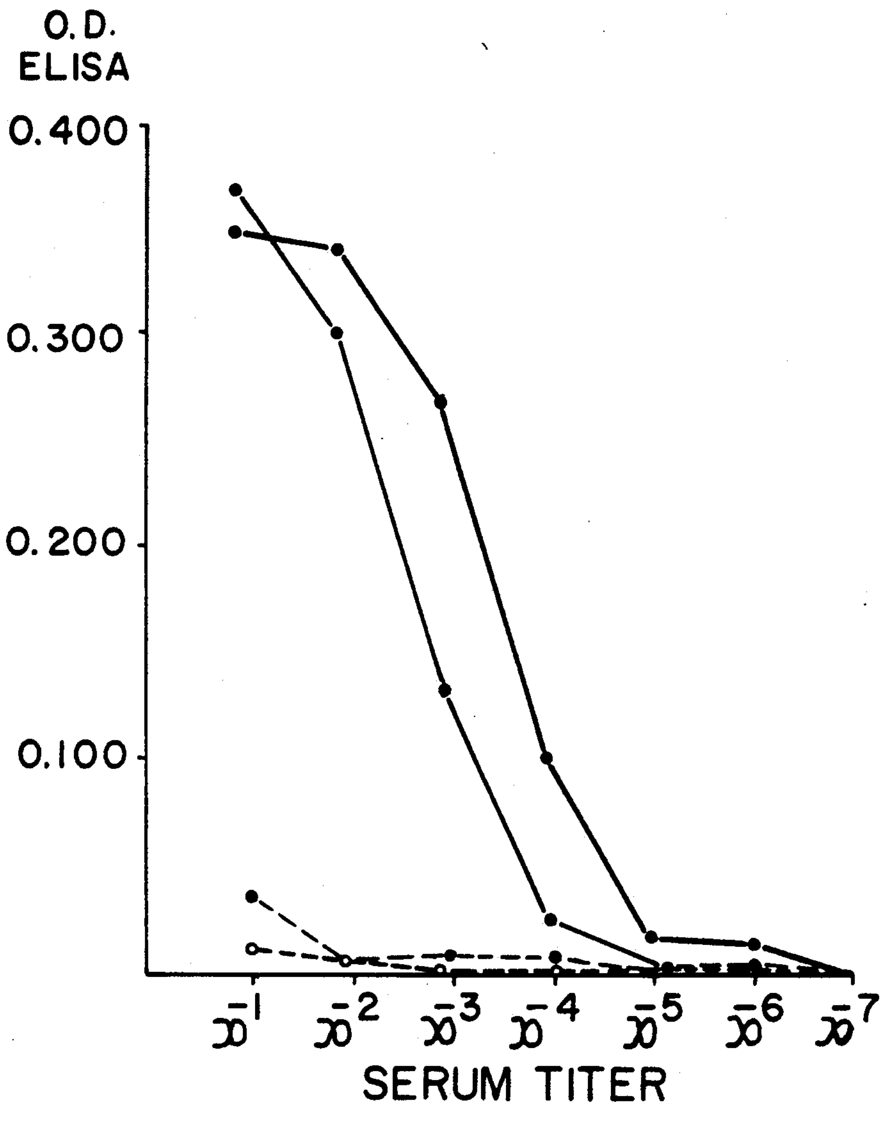
FIG. 6 is an illustration of antibody titers of mice immunized with FA-14 MAP in complete Freund's adjuvant.
Figure 7:
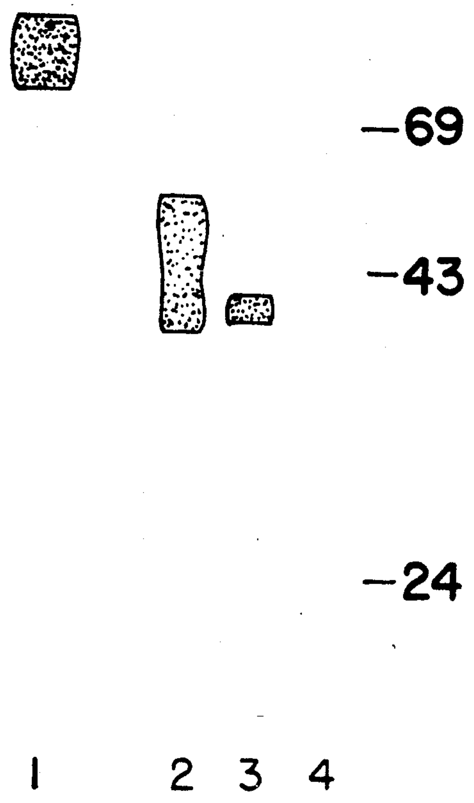
FIG. 7 is an illustration of Immunoprecipitation by rabbit antipeptide serum.

The results of the ELISA are shown in FIG. 6. In FIG. 6, antibody titers between 1,000 to 100,000 were found in mice immunized with FA-14 MAP in complete Freund's adjuvant (two immunizations). This is represented by black circles. The antibody titers between 1,000 and 10,000 were found in mice immunized with FA-14 MAP in alum (two immunizations). This is represented by the white circles. A control antiserum obtained from a T-cell leukemia (represented by broken line and white circles) does not show any cross-reactivity to FA-14 MAP. Another control antiserum pooled from serum obtained from 50 unimmunized mice did not show immunoreactivity (represented by broken line and black circles).

EXAMPLE 15

Asp-Gly-Ile-Ser-Ala-Ala-Lys-Asp-Val, corresponding to the $B_o$ protein of Dane, et al [Science (1984) 225: 593] was synthesized according to the procedures of the previous examples. It produced a high antibody titer in rabbits, and was reactive to its cognate protein as shown by immunoblotting techniques. It has been called DV-9 MAP.

As a MAP molecule it is more precisely defined as (Asp-Gly-Ile-Ser-Ala-Ala-Lys-Asp-Val)$_8$-Lys$_4$-Lys$_2$-Lys-Gly-OH

EXAMPLE 16

General Methods for the Synthesis of Di-epitope Multiple Antigen Peptides Containing -T-cell and B-cell Antigens (a) Method A. Linking Two epitopes on Tanden The synthesis of di-epitope MAPS was accomplished manually by a stepwise solid-phase procedure on Boc-Ala-OCH$_2$-Pam resin (0.1 mmol of Ala is present in 1 g of resin) similar to those mono-epitopes MAPS described in the previous examples. After the removal of the Boc group by 50% TFA and neutralization of the reesulting salt by DIEA, the synthesis of the first level of the carrier core to form Boc-Lys(Boc)-Ala-OCH$_2$-Pam resin was achieved using a 4 mole excess of Boc-Lys(Boc) via DCC alone in $CH_2Cl_2$. The second and third level were synthesized by the same protocol, to give the octabranching Boc-Lys(Boc) core matrix. From this point onward, the synthesis of peptide antigens or two epitopes proceeded as those of the previous examples using the tertbutoxycarbonyl/benzyl protecting group strategy since they were arranged in tandem and were treated as if they are one antigen. Spacers such as tetra-peptide Gly-Pro-Pro-Gly are sometimes inserted between two peptideantigens to allow flexibility. After completion of the synthesis, the MAP-resin was treated with TFA to remove the N$^\alpha$-Boc groups, then acetylated with 10% acetic anhydride/10% DIEA in $CH_2Cl_2$, and finally cleaved with the low-high HF method to remove the MAP from the resin support. The crude peptide was then washed with cold ether/-mercaptoethanol (99:1 vol/vol) to remove p-thiocresol and p-cresol, and extracted into 8M urea in 0.1M Tris.HCl buffer (pH 8.0). To remove the remaining aromatic by-products generated in the cleavage step, MAPs were dialyzed (Spectra Por 6, molecular weight cut off 1,000) in 8M urea and then in 0.1M acetic acid twice for 5–6 hours to remove the urea. The MAPs were lyophilized from $H_2O$ three times to remove acetic acid.

(b) Method B. Linking Two or More Epitopes by Alternating Branching of the Amino groups of Lysines Because there are two amino groups in lysine and because these two amino groups could be protected selectively, the core matrix could be synthesized in such a way to produce that the N$^\alpha$—NH$_2$ group is protected with the acid-labeile Boc group and the N$^\alpha$—NH$_2$ group is protected with the base-labile Fmoc (fluorenylmethoxycarbonyl) group, or vice versa, i.e. N$^\alpha$—NH$_2$ group is protected by the Fmoc group, and the N$^\alpha$—NH$_2$ group is protected by the Boc group. To acheive the synthesis of this core matrix using this selectivity, a core matrix containing N$^\alpha$—$NH_2$—Boc and N$^\alpha$—NH$_2$—Fmoc is illustrated. The synthesis of the core matrix was similar to those described in the previous examples using the Boc-Lys(Boc) for the branching for the first and second level. At the third level, Fmoc-Lys(Boc) was used for the Lys branching of the core to give for each Lys(Boc) and Fmoc-Lys end groups. The synthesis of the first epitope (or two epitopes in tandem) used the Boc/benzyl chemistry as described in the previous examples, but during this synthesis, neutralization time was reduced to 1 min to minimize the premature cleavage of the Fmoc group. The synthesis of the second epitope used the Fmoc/tertbutyl chemistry (i.e. the N$^\alpha$—NH$_2$ group is protected with Fmoc and the side chain is protected with tertbutyl alcohol derived protecting groups) and started after the completion of the first epitope using the Boc-amino acid chain was assembled. The Fmoc-amino acids were used with the side chain protecting groups for the trifunctional amino acids as follows: Glu(OBu$^t$), Asp(OBu$^t$), Lys(Boc) Thr(Bu$^t$), Ser(Bu$^t$), Tyr(bu$^t$), Arg(Pmz), His(Trt), Trp(For), and Cys(Bu$^t$). Repetitive deprotection of N$^\alpha$—Fmoc was by 20% piperidine in dimethylformamide and was preceded by one piperidine prewash and the coupling was mediated with in DMF. After completion of synthesis, the MAP resin was treated with low-high HF to remove the peptide chains from the resin. The workup and purification was essentially the same as those described in the previous examples. The procedure for assembling the peptide chain using the Fmoc.-tertbutyl chemistry was as follows: (1) 20 ml DMF (3×1 min); (2) 20 ml piperidine/DMF (1:1 vol/vol()1 min); (3) 20 ml piperidine/DMF (1:1 vol/vol) (10 min); (4) 20 ml DMF (3×1 min); (5) 20 ml $CH_2Cl_2$(3×1 min); (6) 20 ml DMF (2×1 min); (7) amino acid (4 equiv) in DMF 5 ml (5 min), HOBt(4 equiv) in DMF, DCC(4 equiv) in $CH_2Cl_2$ were added for 2 h; (8) 20 ml DMF (4×2 min); (9) 20 ml $CH_2Cl_2$(2×2 min).

(c) Method C. Linking Two or More Epitopes via Disulfide Linkage of Two Preformed Heterologous MAPS To link two or more epitopes together via disulfide linkage of two preformed MAPS, a dipeptide such as Cys(Acm)-Ala is added at the carboxy terminus of the preformed MAPS. This could be achieved conveniently before the start of the synthesis of the core matrix by adding Boc-Cys(Acm) to the Boc-Ala-$OCH_2$-Pam-resin. After the formation of the dipeptide Boc-Cys(Acm)-Ala-$OCh_2$-Pam-resin, the synthesis of the core matrix, the incorporation of one or more peptide antigen(s) using the procedures described above proceeded to give the preformed MAPS containing a Cys-(Acm)-Ala dipeptide COOH-tail. The cys0Acm) is stable to the HF deprotection method. The preformed MAPS containing the COOH Cys(Acm)-Ala dipeptide tail were purified. The dimerization of two heterologous preformed MAPs was achieved by oxidation with $I_2$ to the disulfide, and which also concommitantly remove the Acm-group from the cysteinyl residue. A detailed procedure was as follows. To 1 mmol of MAP, the heterologous preformed di-epitope MAPs containing Cys(Acm) was dissolved in a de-aerated and $N_2$-purified 50% acetic acid solution at room temperature, 50 ml of a solution of $I_2$ in MeOH(1M solution) was added batchwise for 1 hour at 0° C. The reaction was quenched by adding 1M aqueous sodium thiosulfate (or ascorbic acid) until the yellow color was removed. MeOH was removed by dialysis in 0.1 acetic acid and the desired MAPs were purified by gel permeation chromatograpy, ion-exchange chromatography or reverse-phase high pressure liquid chromatography.

EXAMPLE 17

Synthesis and Purification of a Di-epitope MAPs Containing a Peptide Antigen Leu-Gln-Asp-Pro-Arg-Val-Arg-Gly-Leu-Tyr-Phe-Pro-Ala-Gly-Gly and Another Peptide Antigen $(Thr\text{-}Lys\text{-}Pro\text{-}Thr\text{-}Asp\text{-}Gly\text{-}Asn)_2$ Derived from Hepatitis Surface Coat Antigen and Arranged in an Alternating Branching Method The first peptide antigen, Leu-Gln-Asp-Pro-Arg-Val-Arg-Gly-Leu-Tyr-Phe-Pro-Ala-Gly-Gly, a T-cell promoter was derived from Pre(S)2 residues 12–26, and the second peptide antigen, Thr-Lys-Pro-Thr-Asp-Gly-Asn, a T-cell promoter was derived from the S-protein (S-gene) residues 140–146.

The synthesis was initiated with 0.5 g Boc-Ala-$OCH_2$-Pam-resin at a substitution level of 0.1 mmol/g of resin. The synthesis of the di-lysine and the tetra-lysine was achieved as described in the previous examples using Boc-Lys(Boc) at each level. At the third level, i.e. at the tetra-lysine stage, Fmoc-Lys(Boc) (4 equivalent, 2 mmol) was used for the coupling reaction in the presence of HOBt in DMF for 1 hr. To ensure the reaction would proceed to completion, a double coupling protocol was used (same coupling reaction repeated again). Quantitative ninhyrin test (Sarin, V. K., Kent, S. B. H., Tam, J. P. and Merrifield, R. B. Anal, Biochem. 117, 147–157 (1981)) revealed that the reaction proceeded to greater than 99.73% completion. The synthesis of the first peptide antigen from the pre(S)-2 sequence residues 12–26 was synthesized using the Boc/benzyl chemistry as described in Example 20. The specific protecting groups used in this synthesis were as follows: Asp(OBzl), Arg(Tos), Tyr(BrZ), Thr(Bzl), and Lys(CIZ). Each residue was coupled by the double coupling protocol using the preformed HOBt method as described above and the extend of the coupling was monitored by the quantitative ninhydrin test. Only when the coupling efficency gave 99.7%, was the reaction allowed to proceed to the next cycle. When the coupling reaction was lower 99.7%, a third or fourth coupling using the preformed symmetrial anhydride was used in a different solvent. At the completion of the antigen from the pre(S)-2 sequence, the Fmoc group of the $N^\alpha$—$NH_2$ was then removed by piperidine (20% by volume in DMF). The synthesis of the second antigen derived from the S-protein residues 140–146 was carried out in the Fmoc/tertbutyl chemistry as described in Example 20b. The specific protecting groups were as follows: Thr($Bu^t$), Lys(Boc), and Asp($OBu^t$). All couplings were mediated by the preformed HOBt ester (4 equivalent) and a double coupling protocol was used. The coupling efficency was monitored by the quantitative ninhydrin test and a coupling efficency of 99.7% was achieved. At the completion of the synthesis, the Fmoc-group was removed by piperidine/DMF and the resulting $N^\alpha$—$NH_2$ groups were acetylated by acetic anhydride (10% by volume in $CH_2Cl_2$) in the presence of DIEA for 20 min. The di-epitope MAP (0.3 g) was treated with the low-high HF method as described in previous examples. The di-epitope MAP was extracted from the resin after the HF cleavage in 100 ml of 8M urea, pH 8.2, in 0.1M Tris. HCl and dialyzed in the same buffer (2 liter) in a dialysis bag (M.W. cut off 1,000) for 14 hr. The dialysis continued in 0.1M acetic acid (21×3 times) and the crude product was lyophilized. Amino acid analysis revealed the following molar ratio: Asp 5.0 (5), Thr 4.04(4), Glu 1.05 (1), Pro 4.81 (4), Gly 4.20 (5), Ala 1.25 (1.25), Val 1.02 (1), Leu 2.07 (2), Tyr 0.76 (1), Phe 1.09 (1), Lys 3.22 (3.75), Arg 2.00 (2), which was in agreement with those expected values shown in parenthesis.

EXAMPLE 18

Synthesis and Purification of a Di-epitope MAPs Linked Together by Disulfide Bonds of Two Preformed MAPs Containing Peptide Antigen Leu-Gln-Asp-Pro-Arg-Val-Arg-Gly-Leu-Tyr-Phe-Pro-Ala-Gly-Gly (PreS(2) Sequence 12-26) and Peptide Antigen $(Thr\text{-}Lys\text{-}Pro\text{-}Thr\text{-}Asp\text{-}Gly\text{-}Asn)_2$(S-protein, 140–146) Dervied from the Hepatitis Surface Antigen The two peptide antigens were derived from two preformed MAPs containing a COOH Cys(Acm)-Ala dipeptide tail. The synthesis of each MAP and the oxidative coupling via the disulfide bond was conducted as follows.

The synthesis of the first MAP containing the PreS(2) sequence residues 12–16 was initiated using Boc-Ala-$OCH_2$-Pam resin (0.1 mmol/g substitution) and Boc-Cys(Acm) was coupled to the deprotected Ala-$OCH_2$-Pam resin using the Boc/benzyl chemistry described in previous examples. The core matrix containing the octabranching lysines were synthesized as described in Example 19 using Boc-Lys(Boc). The peptide antigen was then assembled on the octabranched core matrix containing the Cys(Acm)-Ala at the COOH tail. At the completion of the peptide antigen synthesis, the peptide resin was treated with the low-high HF, extracted and dialyzed. Amino acid analysis (after hydrolysis by 6N HCl) gave the following molar ratio: Asp 1.19 (1), Glu 1.05 (1), Pro 2.09 (2), Gly 3.54 (3), Ala 1.17 (1.13), Val 0.80 (1), Leu 1.99 (2), Tyr 0.83 (1), Phe 1.0 (1), Lys 1.09 (0.87), Arg 1.86 (2) which was in agreement with those expected theoretical values shown in parenthesis.

The synthesis of the second MAPs containing the antigen of the S-protein residues 140–146 was carried out in the same manner as those of the first MAPs using the Boc/benzyl chemistry on Boc-Ala-$OCH_2$Pam-resin (0.1 mmol/g substitution). Boc-Cys(Acm) was then coupled to the deprotected Ala-$OCH_2$-Pam-resin before the synthesis of the cotabranching matrix and the peptide antigen. The peptide antigen MAP was cleaved and purified as described in the first MAP described above. Amino acid analysis gave the following molar ratio: Asp 3.79 (4), Thr 2.79 (4), Pro 2.0 (2), Gly 2.0 (2), Lys 2.81 (2.87) which was in agreement with those expected theoretical values shown in parenthesis.

The two preformed MAPs, 1 mmol each were dissolved in 50% acetic acid solution at 22° C. which had been de-aerated and purged with $N_2$. A 50 μl solution of $I_2$ (1M) in methanol was added in batchwise to the acetic solution and the reaction was quenched in 1 hour, after the solution had been chilled to 4° C. by sodium thiosulfite (or ascorbic acid) until the yellow disappeared. The methanol was removed in vaccuo and the solution was dialyzed in 0.1% acetic acid and purified by gel permeation chromatography. The expected product containing two epitopes gave the following amino acid ratio after being hydrolyzed by 6N HCl: Asp 5.0 (5), Thr 2.91 (4), Glu 0.97 (1), Pro 4.11 (4), Gly 5.09 (5), Ala 1.20 (1.25), Val 0.9 (1), Leu 1.92 (2), Tyr 0.77 (1), Phe 1.00 (1), Lys 3.58 (3.75), Arg 1.84 (2) whioch was in agreement with those expected theoretical values shown in parenthesis. and Immunization and Assays. Rabbits (New Zealand White, two for each antigen) were immunized by subcutaneous injection (0.5 ml) of the MAP (0.5 mg in 1 ml of phosphage-buffered saline) in complete Freund's adjuvant (1:1) on day 0 and in incomplete Freund's adjuvant (1:1) on days 21 and 42, and were bled on day 499. The antisera were used without purification.

An enzyme-linked immunoabsorbent assay (ELISA)-was used to test antisera for ability to react with the MAP used for immunization. Peptide antigen (0.5 μg per wel) in carbonate/bicarbonate buffer, pH 9.0, was incubated at 4° C. overnight in a 96-well microtiter plate before being washed. Rabbit antiserum (serially diluted in 0.01M phosphate-buffered saline) was incubated with the microtiter plate-bound antigen for 2 hours at 20° C. and then washed with phosphate-buffered saline. Goat anti-rabbit IgG horseradish peroxidase conjugate was then added and incubated for an additional hour. After washing with phosphate-buffered saline, the bound conjugate was reacted with chromogen (*o*-dianisidine dihydrochloride) at 1 mg/ml in 0.01M phosphate buffer, pH 5.95, for 0.5 hours, and the absorbance of each well was determined with a micro-ELISA reader.

What is claimed is:

1. An antigenic product comprising a dendritic homopolymer containing up to 10 monomeric residues to which a plurality of antigenic molecules are joined by covalent bonds.

2. An antigenic product comprising a dendritic homopolymer containing up to 10 monomeric residues the core molecule of which contains at least two amino groups to which polyamide branches are joined through peptide bonds, said branches having terminal functional groups which are covalently bonded to antigenic molecules.

3. The antigenic product of claim 1 wherein the core molecule is lysine.

4. The antigenic product of claims 1, 2 or 3 wherein the antigenic molecules are identical.

5. The antigenic product of claims 1, 2 or 3 wherein the antigenic molecules are different.

6. The antigenic product of claims 1, 2 or 3 wherein the antigenic molecules are a combination of T-cell and B-cell antigens.

7. (Phe-Glu-Pro-Ser-Glu-Ala-Glu-Ile-Ser-His-Thr-Gln-Lys-Ala)$_8$-Lys$_4$-Lys$_2$-Lys-Gly-OH.

8. ((Asn-Ala-Asn-Pro)$_4$)$_8$Lys$_4$-Lys$_2$-Lys.

9. (Ile-Glu-Asp-Asn-Glu-Tyr-Thr-Ala-Arg-Gln-Gly)$_8$-Lys$_4$-Lys$_2$-Lys-Gly-OH.

10. (Tyr-Ile-Gln-His-Lys-Leu-Gln-Gln-Glu-Ile-Arg-His-Ser-Pro)$_8$-Lys$_4$-Lys$_3$-Lys-Gly-OH.

11. (Asp-Gly-Ile-Ser-Ala-Ala-Lys-Asp-Val)$_8$-Lys$_4$-Lys$_2$-Lys-Gly-OH.

12. An antigenic product comprising a dendritic hompolymer containing up to 10 monomeric residues to which a malarial antigenic peptide is joined by a covalent bond.

13. An antigenic product comprising a dendritic homopolymer containing up to 10 monomeric residues the core molecule of which contains at least two amino groups to which polyamide branches are joined through peptide bonds, said branches having terminal functional groups to which a malarial antigenic peptide is joined by covalent bonds.

14. The antigenic product of claim 12 or 13 wherein the antigenic peptide is selected from the group consisting of:

H-(ASN-Ala-ASN-Pro)$_n$-OH wherein n is 3,

H-(Gly-Asp-Arg-Ala-Asp-Gly-Gln-Pro-Ala)$_n$-OH wherein n is 2,

Glu-Gln-Asn-Val-Glu-His-Asp-Ala,

Asn-Ala-Glu-Asn-Lys-Glu-Glu-Leu-Thr-Ser-Ser-Asp-Pro-Glu-Gly-Gln-Ile-Met.

15. An antigenic product comprising a dendritic homopolymer containing up to 10 monomeric residues to which an hepatitis antigenic peptide is joined by a covalent bond.

16. An antigenic product comprising a dendritic homopolymer containing up to 10 monomeric residues the core molecule of which contains at least two amino groups to which polyamide branches are joined through peptide bonds, said branches having terminal functional groups to which an hepatitis antigenic peptide is joined by a covalent bond.

17. The antigenic product of claim 15 or 16 wherein the antigenic peptide is selected from the group consisting of:

Met-Gln-Trp-Asr-Ser-Thr-Ala-Phe-His-Gln-Thr-Leu-Gln-Asp-Pro-Arg-Val-Arg-Gly-Leu-Try-Leu-Tyr-Leu-Pro-Ala-Gly-Gly,

Asp-Pro-Arg-Val-Arg-Gly-Leu-Tyr-Phe-Pro-Ala-Gly-Gly-Ser-Ser-Ser-Gly-Thr-Val and

Cys-Thr-Lys-Pro-Thr-Asp-Gly-Asn-Cys-Thr-Cys.

18. An antigenic product comprising a dendritic homopolymer containing up to 10 monomeric residues to which a streptococcus antigenic peptide is joined by a covalent bond.

19. An antigenic product comprising a dendritic homopolymer containing up to 10 monomeric residues the core molecule of which contains at least two amino groups to which polyamide branches are joined through peptide bonds, said branches having terminal functional groups to which a streptococcus antigenic peptide is joined by a covalent bond.

20. The antigenic product of claim 18 or 19 wherein the antigenic peptide is:

Asn-Phe-Ser-Thr-Ala-Asp-Ser-Ala-Lys-Ile-Lys-Thr-Leu-Glu-Ala-Glu-Lys-Ala-Asp-Leu-Gly-Lys-Ala-Leu-Gly-Ala.

21. An antigenic product comprising a dendritic homopolymer containing up to 10 monomeric residues to which a polivirus antigenic peptide is joined by a covalent bond.

22. An antigenic product comprising a dendritic homopolymer containing up to 10 monomeric residues the core molecule of which contains at least two amino groups to which polyamide branches are joined through peptide bonds, said branches having terminal functional groups to which a poliovirus antigenic peptide is joined by a covalent bond.

23. The antigenic product of claim 21 or 22 wherein the antigenic peptide is selected from the group consisting of:

Tyr-Ser-Thr-Leu-Ryr-Arg-Trp-Leu-Asp-Aso-Ser-Phe and

Asn-Ala-Pro-Ser-Lys-Thr-Lys-Leu-Glu-Pro-Ser-Ala-Phe.

24. An antigenic product comprising a dendritic homopolymer containing up to 10 monomeric residues to which a foot and mouth disease antigenic peptide is joined by a covalent bond.

25. An antigenic product comprising a dendritic homopolymer containing up to 10 monomeric residues the core molecule of which contains at least two amino groups to which polyamide brances are joined through peptide bonds, said branches having terminal functional groups to which a foot and mouth disease antigenic peptide is joined by a covalent bond.

26. The antigenic product of claim 24 or 25 wherein the antigenic peptide is selected from the group consisting of:

Gly-Ser-Gly-Val-Arg-Gly-Asp-Ser-Gly-Ser-Leu-Ala-Leu-Arg-Val-Ala-Arg-Gln-Leu-Pro and Arg-His-Lys-Gln-Lys-Ile-Val-Ala-Pro-Val-Lys-Gln-Thr-Leu.

27. An antigenic product comprising a dendritic homopolymer containing up to 10 monomeric residues to which an influenza virus antigenic peptide is joined by a covalent bond.

28. An antigenic product comprising a dendritic homopolymer containing up to 10 monomeric residues the core molecule of which contains at least two amino groups to which polyamide branches are joined through peptide bonds, said branches having terminal functional groups to which an influenza virus antigenic peptide is joined by a covalent bond.

29. The antigenic product of claim 27 or 28 wherein the antigenic peptide is selected from the group consisting of:

Gly-Lue-Phe-Gly-Ala-Ile-Ala-Gly-Phe-Ile-Glu and

Arg-Ser-Lys-Ala-Phe-Ser-Asn-Cys-Tyr-Pro-Tyr-Asp-Val-Pro-Asp-Tyr-Ala-Ser.

30. An antigenic product comprising a dendritic homopolymer containing up to 10 monomeric residues to which HIV antigenic peptide is joined by a covalent bond.

31. An antigenic product comprising a dendritic homopolymer containing up to 10 monomeric residues the core molecule of which contains at least two amino groups to which polyamide branches are joined through peptide bonds, said branches having terminal functional groups to which HIV antigenic peptide is joined by a covalent bond.

32. The antigenic product of claim 30 or 31 wherein the antigenic peptide is:

Arg-Ile-Leu-Ala-Val-Glu-Arg-Tyr-Leu-Lys-Asp-Gln-Gln-Leu-Leu-Gly-Ile-Trp-Gly-Cys-Ser.

33. An antigenic product of claim 1 or 2 in which the antigenic molecule is a peptide.

* * * * *